United States Patent [19]

Cassal et al.

[11] Patent Number: 4,675,328
[45] Date of Patent: Jun. 23, 1987

[54] PHENYL-PYRIDINIUM SALTS AND USE THEREOF IN INHIBITING INTESTINAL RESORPTION

[75] Inventors: Jean-Marie Cassal, Mulhouse, France; Albrecht Edenhofer, Riehen; Henri Ramuz, Birsfelden, both of Switzerland

[73] Assignee: Hoffmann-LaRoche Inc., Nutley, N.J.

[21] Appl. No.: 819,187

[22] Filed: Jan. 15, 1986

Related U.S. Application Data

[62] Division of Ser. No. 817,638, Jan. 10, 1986.

[30] Foreign Application Priority Data

Jan. 16, 1985 [CH] Switzerland ............... 187/85

[51] Int. Cl.[4] .................. C07D 211/72; C07D 213/69; C07D 211/84; C07D 213/78
[52] U.S. Cl. .................................. 514/345; 546/291; 546/296; 546/298; 546/300; 546/301; 546/314; 546/315; 546/328; 546/329; 546/333; 546/334; 546/335; 546/337; 546/342; 546/343; 546/344; 546/347; 546/348; 546/346; 546/330; 514/346; 514/348; 514/350; 514/351; 514/354; 514/355; 514/357
[58] Field of Search ............... 546/291, 296, 298, 300, 546/301, 314, 315, 328, 329, 333, 334, 335, 337, 342, 343, 344, 347, 348, 346, 330; 514/345, 346, 348, 350, 351, 354, 355, 357

[56] References Cited

U.S. PATENT DOCUMENTS

| | | | |
|---|---|---|---|
| 3,316,272 | 4/1967 | Roberts et al. | 546/240 |
| 3,374,232 | 3/1964 | de Stevens et al. | 544/333 |
| 3,997,519 | 12/1976 | Armbruster | 546/334 |
| 4,134,982 | 1/1979 | Wise et al. | 514/345 |
| 4,146,637 | 3/1979 | Metz et al. | 546/291 |
| 4,175,195 | 11/1979 | Harris et al. | 546/339 |

FOREIGN PATENT DOCUMENTS

| | | | |
|---|---|---|---|
| 772190 | 7/1971 | Belgium | 546/346 |
| 32837 | 7/1981 | European Pat. Off. | 546/329 |
| 55870 | 7/1982 | European Pat. Off. | 546/344 |
| 2365309 | 5/1974 | Fed. Rep. of Germany | 546/342 |
| 2917131 | 11/1979 | Fed. Rep. of Germany | 546/296 |
| 1271014 | 6/1957 | France | 546/291 |
| 5169360 | 10/1963 | Japan | 546/328 |
| 5169460 | 10/1963 | Japan | 546/347 |
| 1647968 | 7/1968 | Japan | 546/339 |
| 6145273 | 11/1981 | Japan | 546/337 |
| 57-108276 | 7/1982 | Japan | 546/333 |
| 57-108277 | 7/1982 | Japan | 546/342 |
| 992157 | 5/1965 | United Kingdom | 546/314 |
| 1404868 | 9/1975 | United Kingdom | 546/330 |
| 2038816 | 7/1980 | United Kingdom | 546/344 |
| 2038825 | 7/1980 | United Kingdom | 546/328 |
| 2039218 | 8/1980 | United Kingdom | 546/301 |

OTHER PUBLICATIONS

Glover, G., et al., Aromatic Esters which Inhibit Plasmin or Thrombin by Formation of Relatively Stable Acyl Enzymes, J. Med. Chem. 1973, 16(3), 262-6 (Chem Abst. 78:155152k).
Pyridinium Salts, SA5713613, Pub. Oct. '67 (Derwent 30115).
Dubenko, R. G., et al., Thiazolium Bromides, Organic Chem. Inst. Acad. Sci. Ukr.; 12/68 (Derwent 38526).

Primary Examiner—John M. Ford
Assistant Examiner—Robert C. Whittenbaugh
Attorney, Agent, or Firm—Jon S. Saxe; Bernard S. Leon; Mark E. Waddell

[57] ABSTRACT

Polycyclic salts of the formula

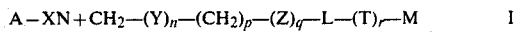

wherein
  $A^-$ is the anion of a strong organic or inorganic acid;
  $XN^+$ is pyridinium, pyrimidinium, thiazolium or imidazolium substituted by $R^1$, $R^2$ and $R^3$;
  n, q and r individually are the integer 1 or 0 and p is an integer from 1 to 15;
  Y is $CH_2$, $C(H,OH)$ or $C(O)$:
  Z is O, S, $CH_2$, $C(O)$, $NQ^1$, $SO_2$, $C(O)O$, $OC(O)$, $C(O)N(Q^1)$ or $N(Q^1)C(O)$;
  L is p-phenylene substituted by $R^4$; and
  M is phenyl substituted by $R^5$ and $R^6$,
  T has one of the meanings given above, for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
  $R^1$ is a group Ar, Ar-$C_{1-4}$-alkyl, ArO or ArC(O),
  Ar is phenyl substituted by $R^7$, $R^8$ and $R^9$;
  $R^2$ and $R^3$ individually are H, $C_{1-4}$-alkyl, $C_{1-4}$-alkoxy or $C_6H_5$, with the proviso that the N-atom in the 3-position of an imidazolium group $XN^+$ is substituted by Ar, Ar-$C_{1-4}$-alkyl or $C_{1-4}$-alkyl,
  $R^4$, $R^5$, $R^6$, $R^7$, $R^8$ and $R^9$ individually are H, halogen, $CF_3$, $NO_2$, CN, $C_{1-4}$- -(alkyl, alkoxy, alkylthio or alkylsulphonyl), $SO_2N(R,Q)$, $C(O)N(Q^4,Q^5)$, $C(O)Q^4$, $C(O)OQ^4$ or $OC(O)Q^4$,
  R, Q, $Q^1$, $Q^2$ and $Q^3$ individually are H or $C_{1-4}$-alkyl, and
  $Q^4$ and $Q^5$ individually are $C_{1-4}$-alkyl inhibit the intestinal resorption of cholesterol and of bile salts in the enterohepatic circulation. These salts containing a quaternary N-atom can be manufactured starting from corresponding amines.

18 Claims, No Drawings

PHENYL-PYRIDINIUM SALTS AND USE THEREOF IN INHIBITING INTESTINAL RESORPTION

BACKGROUND

This application claims priority under 35 USC 120 based on copending U.S. application Ser. No. 817,638, filed Jan. 10, 1986.

The present invention is concerned with phenyl-pyridinium salts, their pharmaceutical preparations and a process for their manufacture.

SUMMARY OF THE INVENTION

The inventive salts have the formula

wherein $A^-$ is an anion of a strong organic or inorganic acid;
$XN^+$ is pyridinium, pyrimidinium, thiazolium or imidazolium substituted by $R^1$, $R^2$ and $R^3$;
n, q and r individually are the integer 1 or 0 and p is an integer from 1 to 15;
Y is $CH_2$, C(H,OH) or C(O):
Z is O, S, $CH_2$, C(O), $NQ^1$, $SO_2$, C(O)O, OC(O), C(O)N($Q^1$) or N($Q^1$)C(O);
L is p-phenylene substituted by $R^4$; and
M is phenyl substituted by $R^5$ and $R^6$,
T has one of the meanings given above for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
$R^1$ is a group Ar, Ar—$C_{1-4}$—alkyl, ArO or ArC(O),
Ar is phenyl substituted by $R^7$, $R^8$ and $R^9$;
$R^2$ and $R^3$ individually are H, $C_{1-4}$—alkyl, $C_{1-4}$—alkoxy or $C_6H_5$,
with the proviso that the N-atom in the 3-position of an imidazolium group $XN^+$ is substituted by Ar,
Ar—$C_{1-4}$—alkyl or $C_{1-4}$—alkyl,
$R^{4'}$, $R^5$, $R^6$, $R^7$, $R^8$ and $R^9$ individually are H, halogen, $CF_3$, $NO_2$, CN, $C_{1-4}$—(alkyl, alkoxy, alkylthio or alkylsulphonyl), $SO_2N(R,Q)$, $C(O)N(Q^4, Q^5)$, $C(O)Q^4$, C(O)O$Q^4$ or OC(O)$Q^4$,
R, Q, $Q^1$, $Q^2$ and $Q^3$ individually are H or $C_{1-4}$—alkyl, and
$Q^4$ and $Q^5$ individually are $C_{1-4}$—alkyl.

The salts of formula I possess valuable pharmacological properties. In particular, they inhibit the intestinal resorption of cholesterol and of bile salts in the enterohepatic circulation. Accordingly, they can be used in the treatment, control or prevention of illnesses such as hypercholesterolaemia, atherosclerosis of obesity.

DETAILED DESCRIPTION OF THE INVENTION

The present invention is concerned with novel polycyclic salts, a process for their manufacture and medicaments based on these salts.

The salts have the formula

wherein $A^-$ is an anion of a strong organic or inorganic acid;
$XN^+$ is pyridinium, pyrimidinium, thiazolium or imidazolium substituted by $R^1$, $R^2$ and $R^3$;
n, q and r individually are the integer 1 or 0 and p is an integer from 1 to 15;
Y is $CH_2$, C(H,OH) or C(O):
Z is O, S, $CH_2$, C(O), $NQ^1$, $SO_2$, C(O)O, OC(O), C(O)N($Q^1$) or N($Q^1$)C(O);
L is p-phenylene substituted by $R^4$; and
M is phenyl substituted by $R^5$ and $R^6$,
T has one of the meanings given above for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
$R^1$ is a group Ar, Ar—$C_{1-4}$—alkyl, ArO or ArC(O),
Ar is phenyl substituted by $R^7$, $R^8$ and $R^9$;
$R^2$ and $R^3$ individually are H, $C_{1-4}$—alkyl, $C_{1-4}$—alkoxy or $C_6H_5$,
with the proviso that the N-atom in the 3-position of an imidazolium group $XN^+$ is substituted by Ar,
Ar—$C_{1-4}$—alkyl or $C_{1-4}$—alkyl,
$R^{4'}$, $R^5$, $R^6$, $R^7$, $R^8$ and $R^9$ individually are H, halogen, $CF_3$, $NO_2$, CN, $C_{1-4}$—(alkyl, alkoxy, alkylthio or alkylsulphonyl), $SO_2N(R,Q)$, C(O)N($Q^4$, $Q^5$), $C(O)Q^4$, C(O)O$Q^4$ or OC(O)$Q^4$,
R, Q, $Q^1$, $Q^2$ and $Q^3$ individually are H or $C_{1-4}$—alkyl, and
$Q^4$ and $Q^5$ individually are $C_{1-4}$—alkyl.

In the specification, the term "alkyl" denotes straight-chain or or branched-chain alkyl residues of 1 to 12 carbon atoms. The residues denoted by $C_{1-4}$ mentioned herein (e.g., $C_{1-4}$alkyl, $C_{1-4}$alkoxy, $C_{1-4}$alkyl sulphonyl) are straight-chain or branched residues of one to four carbon atoms. Examples thereof are methyl, ethyl, isopropyl, methoxy, methylthio and methylsulphonyl.

Illustratively, C(H,OH) for "Y" denotes hydroxymethylene.

Illustratively, ArC(O) for "$R^1$" denotes aroyl, e.g. benzoyl.

An anion of a strong organic or inorganic acid is derived from the corresponding acid by removal of the cation $H^+$. Examples of anions of strong organic or inorganic acids are $C_{1-1}$-alkylsulphonyloxy, phenylsulphonyloxy and tosyloxy, and $Cl^-$, $Br^-$, $I^-$, $ClO_4^-$, $SO_4^-$, $PO_4^)$ and $NO_3^-$, respectively.

Unless otherwise indicated the formula in the specification with asymmetric carbon atoms are shown as racemates. The salts of formula I can contain one or more asymmetric carbon atoms and can accordingly be present as and the invention encompasses optically active enantiomers, diastereomers as well as mixtures thereof, e.g. racemates of such formula.

The salts of formula I can be hydrated. The hydration can be effected by conventional techniques in the course of the manufacturing process or can occur gradually as a result of hygroscopic properties of an initially anhydrous salt of formula I.

Preferred salts of formula I are those in which $XN^+$ is pyridinium substituted in the para-position by $R^1$, especially those in which $A^-$ is $Cl^-$ or $Br^-$; $XN^+$ is p-phenylpyridinium or p-benzoylpyridinium; p is the integer 1, 2, 8 or 11; q is the integer 1; n and r individually are the integer 1 or 0; Y is CHOH; Z is O, S, NH or C(O)NH; $R^4$, $R^5$ and $R^6$ are H; or $R^4$ is $CH_3$; $R^5$ is F, Cl, Br, $CF_3$, $NO_2$, CN, $OCH_3$ or $SO_2CH_3$ in the para-position to (T)$_r$; and T is C(O), O, S, $SO_2$, $CH_2$, $C_2H_4$, NH, C(O)$CH_2$ or NHC(O).

The following are examples of such preferred salts;
1-[2-Hydroxy-3-[p-(p-nitrobenzoyl)phenoxy]propyl]-4-phenylpyridinium chloride,
1-[12-(p-phenethylphenoxy)dodecyl]-4-phenylpyridinium chloride,
1-[3-[p-[(p-chlorophenyl)thio]phenoxy]-2-hydroxypropyl]-4-phenylpyridinium chloride, 1-[3-[p-(p-cyanobenzoyl)phenoxy]-2-hydroxypropyl]-4-phenylpyridinium chloride and
1-[9-(p-phenethylphenoxy)nonyl]-4-phenylpyridinium bromide.

The salts of formula I can be manufactured by a. reacting the aromatic amine XN which is correspondingly substituted to the cation XN+ with a compound of the formula $$\text{C—CH}_2\text{—(Y)}_n\text{—(CH}_2)_p\text{—(Z)}_q\text{—L—(T)}_r\text{—M} \qquad \text{II}$$

wherein G is a conventional leaving group or forms an epoxide with a hydroxymethylene group Y, or b. reacting a pyrylium salt of the formula $$\text{A}'^-\text{—X}'\text{O}^+ \qquad \text{III}$$

wherein A'− is a BF$_4^-$, ClO$_4^-$ or PF$_6^-$ anion and X'O+ is pyrylium substituted by R$^1$, R$^2$ and R$^3$, with an amine of the formula $$\text{H}_2\text{N—CH}_2\text{—(Y)}_n\text{—(CH}_2)_p\text{—(Z)}_q\text{—L—(T)}_r\text{—M} \qquad \text{IV}$$

wherein XN+, n, p, q, r, Y, Z, T, L and M have the significance given above, and replacing the anion A'− in the salt obtained by A−.

Examples of conventional leaving groups G present in the compounds of formula II are chlorine, bromine, iodine, mesyloxy, phenylsulphonyloxy and tosyloxy. The reaction of an amine XN with a compound II containing a leaving group can be carried out at a temperature up to above the reflux temperature of the reaction mixture, conveniently at about 80° C. or at room temperature (about 23° C.), depending on the reactants used, if desired in a solvent such as an aromatic hydrocarbon, e.g. toluene or benzene, or dimethylformamide (DMF) or acetonitrile.

The reaction of an amine XN with an epoxide II can be carried out in a solvent such as water and dioxan or tetrahydrofuran (THF), in acidic medium (pH less than 8), conveniently in the presence of the acid corresponding to the anion A−, at a temperature up to about the reflux temperature of the reaction mixture, conveniently at about 70° C.

The reaction of a pyrylium salt III with an amine IV can be carried out at a temperature of about 0° C. up to about room temperature, if desired in a solvent such as toluene or DMF.

The compounds of formula II in which (Z)$_q$ is a group Z' having the significance O, S, N(Q$^1$) or OC(O) can be prepared by reacting a compound of the formula $$\text{G—CH}_2\text{—(Y)}_n\text{—(CH}_2)_p\text{—G}' \qquad \text{V}$$

wherein G' is a leaving group, with a compound of the formula $$\text{HZ}'\text{—L—(T)}_r\text{—M} \qquad \text{VI.}$$

Thus, for the preparation of a halide of formula II, such as a bromide, in which e.g. (Z)$_q$ is oxygen, a dibromide of formula V can be reacted with a phenol of formula VI in the presence of a base such as sodium hydroxide in a solvent such as ethanol while heating, e.g. to 80° C. For the preparation of a corresponding epoxide of formula II, a chloroepoxide of formula V, e.g. epichlorohydrin, can be reacted with a phenol VI in the presence of a base such as piperidine at an elevated temperature. For the preparation of an epoxide of formula II in which e.g. (Z)$_q$ is the group NH, a chloroepoxide V can be heated with an aniline derivative of formula VI in the presence of potassium carbonate at an elevated temperature, e.g. under reflux.

The compounds of formula II in which Y is hydroxymethylene, Z is oxygen and G is mesyloxy, phenylsulphonyloxy or tosyloxy can also be prepared starting from the corresponding diols of formula II in which G stands for OH. These diols can be prepared by reacting the corresponding phenols of formula VI with a 3-tosyloxy-1,2-propanediol acetonide and cleaving the dioxolane obtained, e.g. as described in Example 7.

The compounds of formula II in which (Z)$_q$ is S can be oxidized to corresponding compounds II containing a sulphonyl group (Z)$_q$, e.g. by means of M-chloroperbenzoic acid or hydrogen peroxide and acetic acid.

A compound of formula II in which (Z)$_q$ is a group N(Q$^1$)C(O) can be prepared by reacting an amine of the formula $$\text{G—CH}_2\text{—(Y)}_n\text{—(CH}_2)_p\text{—N(H,Q}^1) \qquad \text{VII}$$

with an acid chloride of the formula $$\text{Cl—C(O)—L—(T)}_r\text{—m} \qquad \text{VIII,}$$

e.g. as described for the reaction of an amine XN with a compound II containing a leaving group.

For the preparation of a compound of formula II in which (Z)$_q$ is a group C(O)O or C(O)N(Q$^1$), an acid of the formula $$\text{G—CH}_2\text{—(Y)}_n\text{—(CH}_2)_p\text{—COOH} \qquad \text{IX}$$

or a functional derivative thereof, e.g. an acid chloride or an acid anhydride, can be either esterified with a phenol of the formula $$\text{HO—L—(T)}_r\text{—M} \qquad \text{X}$$

in a manner known per se or reacted with an amine of the formula $$(\text{H,Q}^1)\text{N—L—(T)}_r\text{—M} \qquad \text{XI}$$

in a manner known per se. Thus, e.g. the chloride of an acid of formula IX, e.g. 3-chloropropionyl chloride, can be reacted with an amine of formula XI in a solvent such as chloroform in the presence of a sodium hydroxide solution to give an amide of formula II in which (Z)$_q$ is the group CONH.

The compounds of formula II in which (Z)$_q$ is a carbonyl or methylene group can be prepared in a manner known per se, e.g. by reacting an aldehyde of the formula $$\text{HC(O)—L—(T)}_r\text{—M} \qquad \text{XII}$$

with 1,3-propanedithiol and with butyl lithium, reacting the lithium salt obtained with a halide of formula V in which G' represents halogen and converting the resulting thioketal of the formula

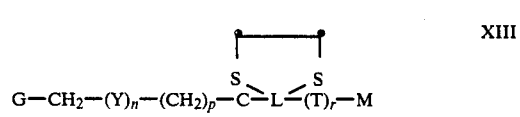

XIII into the corresponding ketone of formula II in which (Z)$_q$ is carbonyl by means of mercury(II) sulphate and methanol or into the corresponding compound of formula II in which $(Z)_q$ is methylene by hydrogenation in the presence of Raney-nickel.

The pyrylium salts of formula III can be prepared in a manner known per se, e.g. starting from the corresponding alpha- or gamma-pyrones or the corresponding 1,5-diketones or 1,5-dialdehydes.

The amines of formula IV can be prepared in a manner known per se, e.g. by reacting a halide of formula II with potassium phthalimide in dimethylformamide and reacting the phthalimide obtained with hydrazine hydrate in ethanol.

Any racemates within formula I can be separated into their enantiomeric and diastereoisomeric components by conventional techniques. For example, the compounds of formula I having asymmetric carbon atoms may be separated into individual stereoisomers by conventional means, such as by the use of an optically active acid as a resolving agent, followed by fractional crystallization from a suitable solvent.

Alternatively any enantiomer of a salt of formula I may be obtained by stereospecific synthesis using optically pure starting materials of known configuration.

The salts of formula I possess valuable pharmacological properties. In particular, they inhibit the intestinal resorption of cholesterol and of bile salts in the enterohepatic circulation. Accordingly, they can be used in the control or prevention of illnesses such as hypercholesterolaemia, atherosclerosis and obesity.

The inhibition of the intestinal resorption of cholesterol can be demonstrated as follows in an animal experiment:

Squirrel monkeys are orally administered the substances to be investigated together with a feed containing a protein, starch, triolein and [26-$^{14}$C]-cholesterol. Thereupon, the faces is collected for 2.5 days. The difference determined between the administered and the excreted radioactive cholesterol in the feces is taken as the measurement of resorbed cholesterol. The cholesterol resorption ("CHORES") is expressed in percentages of the control values determined prior to the medication. The results which have been obtained with some representative products in accordance with the invention are reproduced in the Table hereinafter. There are given for each of the compounds indicated therein the dosage administered (in $\mu$mol/kg p.o.) as well as in each case the cholesterol resorption (CHORES) determined in percentages of the cholesterol resorption in the pre-period. Moreover, the Table contains data concerning the acute toxicity of the compounds investigated, i.e. the toxicity after single oral administration to mice, expressed in dose of the compound at which the animal survives.

TABLE

| Compound of formula I in Example No. | Dosage in $\mu$mol/kg p.o. | CHORES in % of the pre-period | Toxicity in mg/kg p.o. |
|---|---|---|---|
| 1 | 30 | 31 | 5000 |
| 2A)e) | 30 | 45 | 5000 |
| 2A)o) | 30 | 44 | 5000 |
| 4A)d) | 30 | 47 | |
| 4A)e) | 30 | 39 | |

The products in accordance with the invention can be used as medicaments, e.g. in the form of pharmaceutical preparations. Illustratively, the pharmaceutical preparations can be administered orally, e.g. in the form of tablets, coated tablets, dragees, hard and soft gelatine capsules, solutions, emulsions or suspensions.

For the manufacture of pharmaceutical preparations the products in accordance with the invention can be processed with any conventional pharmaceutically inert, inorganic or organic carriers. Lactose, maize starch, talc, stearic acid or its salts can be used e.g. as such carriers for tablets, coated tablets, dragees and hard gelatine capsules. Vegetable oils, waxes, fats, semi-solid and liquid polyols are e.g. suitable as carriers for soft gelatine capsules; depending on the nature of the active substances no carrier is, however, generally required in the case of soft gelatine capsules. Water, polyols, saccharose, invert sugar and glucose are e.g. suitable as carriers for the manufacture of solutions and syrups.

The pharmaceutical preparations can, also contain any conventional preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned earlier, medicaments containing a salt of formula I are also an object of the present invention, as is a process for the manufacture of such medicaments, which process comprises bringing one or more products in accordance with the invention and, if desired, one or more other therapeutically valuable substances into a galenical administration form.

The dosage can vary within wide limits and is, of course, fitted to the individual requirements routes of administration, age weight and condition of mammal in each particular case. In general, in the case of oral administration a daily dosage of about 50 mg to about 3 g, preferably of about 200 mg to about 1 g, of salt I should be appropriate. The dosage can be administered in a single dose or several dosages divided over the day.

In general salt I amounts to about 30% to about 70% by weight of the pharmaceutical compositions.

The following examples illustrate the process for preparing the salts of formula I. Temperatures are expressed in degrees Celsius (°C.) and room temperature is about 23° C. The numbered examples were carried out as written. Example A was not carried out.

EXAMPLE 1

A solution of 2.06 g (6.88 mmol) of 4-(2,3-epoxypropoxy)-4'-nitrobenzophenone in 50 ml of dioxan and 25 ml of water was treated with 1.06 g (6.88 mmol) of 4-phenylpyridine and stirred at 70° C. while adding 1N HCl at a pH less than 8. After stirring at 70° C. for 18 hours the mixture was cooled to 20° C., treated with 300 ml of water and extracted three times with 200 ml of chloroform. The organic phase was dried and concentrated. The residue was recrystallized from acetone. There was obtained 1-[2-hydroxy-3-[p-(p-nitrobenzoyl)phenoxy]propyl]-4-phenylpyridinium chloride in 50% yield, m.p. 240° C.

The epoxide starting material (m.p. 120°–122° C.) was prepared analogously to Example (2B)(a).

EXAMPLE 2

(2A) Analogously to Example 1 there were prepared:
(2A)(a) 1-[3-[p-Fluorobenzoyl)phenoxy]-2-hydroxypropyl-4-phenylpyridinium chloride, m.p. 234° C.;
(2A)(b) 1-[3-[p-(p-chlorobenzoyl)phenoxy]-2-hydroxypropyl]-4-phenylpyridinium chloride, m.p. 220° C.;
(2A)(c) 1-[3-[p-(p-bromobenzoyl)phenoxy]-2-hydroxypropyl]-4-phenylpyridinium chloride, m.p. 180° C.;

(2A)(d) 1-[3-[p-(p-anisoyl)phenoxy]-2-hydroxypropyl]-4-phenylpyridinium chloride, m.p. 207° C.;

(2A)(e) 1-[3-[p-(p-cyanobenzoyl)phenoxy]-2-hydroxypropyl]-4-phenylpyridinium chloride, m.p. 245° C.;

(2A)(f) 1-[3-[(1-benzoyl-o-tolyl)-oxy]-2-hydroxypropyl]-4-phenylpyridinium chloride, m.p. 192° C.;

(2A)(g) 1-[3-(p-benzoyphenoxy)-2-hydroxypropyl]-4-phenylpyridinium chloride, m.p. 201° C.;

(2A)(h) 1-[3-[p-methylsulphonyl)benzoyl]phenoxy]-2-hydroxypropyl]-4-phenylpyridinium chloride, m.p. 148° C.;

(2A)(i) 1-[3-[p-(p-chlorobenzoyl)anilino]-2-hydroxypropyl]-4-phenylpyridinium chloride, m.p. 248° C.;

(2A)(j) 1-[3-[[p-(p-chlorobenzoylphenyl]thio]-2-hydroxypropyl]-4-phenylpyridinium chloride, m.p. 229° C.;

(2A)(k) 1-[3-(p-benzylphenoxy)-2-hydroxypropyl]-4-phenylpyridinium chloride, m.p. 220° C.;

(2A)(l) 1-[3-[p-(chlorophenoxy)phenoxy]-2-hydroxypropyl]-4-phenylpyridinium chloride, m.p. 208° C.;

(2A)(m) 1-[3-(p-anilinophenoxy)-2-hydroxypropyl]-4-phenylpyridinium chloride, m.p. 216° C.;

(2A)(n) 1-[2-hydroxy-3-[p-[(nitrophenyl)thio]phenoxy]-propyl]-4-phenylpyridinium chloride, m.p. 234° C.;

(2A)(o) 1-[3-[p-[(p-chlorophenyl)thio]phenoxy]-2-hydroxypropyl]-4-phenylpyridinium chloride, m.p. 187° C.;

(2A)(p) 1-[3][p-[(p-bromophenyl)sulphonyl]phenoxy]-2-hydroxypropyl]-4-phenylpyridinium chloride, m.p. 223° C.;

(2A)(q) 1-[3-[p-(p-chlorobenzamido)phenoxy]-2-hydroxypropyl]-4-phenylpyridinium chloride, m.p. 216° C.;

(2A)(r) 1-[2-hydroxy-3-(p-phenacylphenoxy)propyl]-4-phenylpyridinium chloride, m.p. 249° C.;

(2A)(s) 1-[3-(4-biphenyloxy)-2-hydroxypropyl]-4-phenylpyridinium chloride, m.p. 204° C.

(2B)(a) The epoxide starting used material for the manufacture of the above product of Example (2A)(f) was prepared as follows:

10.6 g of 4-hydroxy-3-methylbenzophenone, 50 g of epichlorohydrin and 3 drops of piperidine were heated on a steam-bath for 12 hours. The reaction solution was freed from excess epichlorohydrin under reduced pressure. The residue was dissolved in 20 ml of chloroform and, after the addition of 20 ml of 3N sodium hydroxide solution, shaken at room temperature. The organic phase was separated, washed with water and evaporated to dryness. 4-(2,3-Epoxypropoxy)-3-methylbenzophenone crystallized from the oily residue, m.p. 56°-58° C. after recrystallization from ethanol.

(2B)(b) The following epoxide starting materials for Examples (2A)(e) to (2A)(r) were prepared analogously to Example (2B)(a):

p-[p-(2,3-Epoxypropoxy)benzoyl]benzonitrile, m.p. 100°-101° C., Example (2A)(e);

4-(2,3-epoxypropoxy)-4'-(methylsulphonyl)benzophenone, m.p. 165°-167° C., Example (2A)(h);

4-chloro-4'-[(2,3-epoxypropyl)thio]benzophenone, m.p. 94°-95° C., Example (2A)(j);

1-[p-(benzyloxy)phenoxy]-2,3-epoxypropane, m.p. 113°-114° C. (methanol), Example (2A)(k);

1-[p-(p-chlorophenoxy)phenoxy]-2,3-epoxypropane, m.p. 49°-52° C. (ethyl acetate-petroleum ether). Example (2A)(l);

2,3-epoxypropyl p-(p-nitrophenylthio)phenyl ether. m.p. 96°-99° C. (methanol-chloroform). Example (2A)(n);

1-[p-(chlorophenylthio)phenoxy]-2,3-epoxypropane, m.p. 61°-62° C. (isopropyl ether), Example (2A)(o);

p-[(p-bromophenyl)sulphonyl]phenyl 2,3-epoxypropyl ether, m.p. 126°-128° C. (isopropanol), Example (2A)(p);

p-chloro-4'-(2,3-epoxypropoxy)benzanilide, m.p. 181° C. (isopropanol), Example (2A)(q);

4'-(2,3-epoxypropoxy)-2-phenylacetophenone, m.p. 85°-86° C. (isopropanol), Example (2A)(r).

(2B)(c) The epoxide starting material used for the manufacture of the product of Example (2A)(i) was prepared as follows:

23.2 g of 4-chloro-4'-aminobenzophenone, 92 g of epichlorohydrin and 7 g of potassium carbonate were heated at reflux for 15 hours. The excess epichlorohydrin was evaporated in vacuo and the solid residue was partitioned between water and chloroform. From the organic phase there was obtained 4-chloro-4'-[(2,3-epoxypropyl)amino]benzophenone which was recrystallized twice from methanol, m.p. 128°-129° C.

EXAMPLE 3

A solution of 3 g (9.39 mmol) of 1-(3-bromopropoxy)-4-(2-phenethyl)benzene and 5 g of 4-phenylpyridine in 60 ml of toluene was heated at 100° C. for 24 hours and then cooled to 20° C. After filtration and recrystallization from methylene chloride-acetone there was obtained 1-[3-(p-phenethylphenoxy)propyl]-4-phenylpyridinium bromide in 70% yield, m.p. 128° C.

The bromide starting material was prepared as follows:

A solution of 1.4 g of p-(2-phenethyl)phenol in 10 ml of ethanol was added to a solution of 0.282 g of sodium hydroxide in 10 ml of ethanol. After adding 1.44 ml of 1,3-dibromopropane the mixture was heated at 80° C. for 2 hours, left to cool to room temperature and filtered. The filtrate was dried in a rotary evaporator. The residue was purified over silica gel with methylene chloride. There was obtained a colorless oily residue, 1-(3-bromopropoxy)-4-(2-phenethyl)benzene.

EXAMPLE 4

(4A) Analogously to Example 3, (4A)(a) from 3-phenylpyridine there was manufactured 1-[3-(p-phenethylphenoxy)propyl]-3-phenylpyridinium bromide, m.p. 155° C.;

(4A)(b) from 4-phenylpyrimidine there was manufactured 1-[3-(p-phenethylphenoxy)propyl]-4-phenylpyrimidinium bromide, m.p. 169° C.;

(4A)(c) from 4-benzoylpyridine there was manufactured 4-benzoyl-1-[3-(p-phenethylphenoxy)propyl]-pyridinium bromide, m.p. 161° C.;

(4A)(d) from 9-bromononyl p-phenethyl-phenyl ether (m.p. 31° C.) there was manufactured 1-[9-(p-phenethylphenoxy)nonyl]-4-phenylpyridinium bromide, m.p. 147° C.;

(4A)(e) from 12-bromododecyl p-phenethyl-phenyl ether (m.p. 50°-51° C.) there was manufactured 1-[12-(p-phenethylphenoxy)dodecyl]-4-phenylpyridinium bromide, m.p. 120° C.;

(4A)(f) from 1-[p-(3-bromopropoxy)phenyl]-2-phenyl-1-ethanone (m.p. 120° C.) there was manufactured 4-phenyl-1-[3-[p-phenacetyl)phenoxy]propyl]-pyridinium bromide, m.p. 189° C.;

(4A)(g) from 4-(3-bromopropoxy)benzophenone (m.p. 75°-76° C. from methanol) there was manufactured 1-[3-(p-benzoylphenoxy)propyl]-4-phenylpyridinium bromide in the form of an oil;

(4A)(h) from 4-(3-bromopropoxy)-4-chlorobenzophenone (m.p. 73°–75° C. from methanol) there was manufactured 1-[3-[p-(p-chlorobenzoyl)phenoxy]propyl]-4-phenylpyridinium bromide, m.p. 211° C.;

(4A)(i) from 4-(3-chloropropionamido)benzophenone there was manufactured 1-[2-[(p-benzoylphenyl)carbamoyl]ethyl]-4-phenylpyridinium chloride, m.p. 251° C.;

(4A)(j) from 1-(3-bromopropoxy)-4-(p-chlorophenoxy)-benzene (b.p. 155°–160° C. under 0.98 Torr) there was manufactured 1-[3-[p-(p-chlorphenoxy)phenoxy]propyl]-4-phenylpyridinium bromide, m.p. 172° C.;

(4A)(k) from 4-(3-bromopropoxy)-4'-nitrobenzophenone there was manufactured 1-[3-[p-(p-nitrobenzoyl)phenoxy]propyl]-4-phenylpyridinium bromide, m.p. 222° C.;

(4A)(l) from 4-(12-bromododecyloxy)-4'-nitrobenzophenone there was manufactured 1-[12-[(p-nitrobenzoyl)phenoxy]dodecyl]-4-phenylpyridinium bromide, m.p. 126°–127° C.;

(4A)(m) from 4-(3-bromopropoxy)-4'-trifluoromethylbenzophenone there was manufactured 1-[3-[p-(p-trifluoromethylbenzoyl)phenoxy]propyl]-4-phenylpyridinium bromide, m.p. 173°–177° C. p0 (4B) The chloride starting material used for the manufacture of the above product of Example (4A)(i) was prepared as follows:

A solution of 3.95 g of p-aminobenzophenone in 100 ml of chloroform was treated with 2.6 g of 3-chloropropionyl chloride and, after the addition of 26 ml of 1N sodium hydroxide solution, stirred at room temperature. The organic phase was separated, washed in sequence with water, 1N HCl and water, dried and evaporated. After recrystallization from methanol of the oil obtained there was obtained 4-(3-chloropropionamido)-benzophenone, m.p. 135°–136° C.

EXAMPLE 5

By filtering the bromide product of Example 3 through a strongly basic styrene-divinylbenzene (IRA 400) ion exchanger loaded with chloride ions there was obtained 1-[3-(p-phenethylphenoxy)propyl]-4-phenylpyridinium chloride in 95% yield, m.p. 126° C.

EXAMPLE 6

Analogously to Example 5, (6a) from the bromide of Example (4A)(h) there was obtained 1-[3-[p-(p-chlorobenzoyl)phenoxy]propyl]-4-phenylpyridinium chloride, m.p. 196° C.;

(6b) from the bromide of Example (4A)(k) there was obtained 1-[3-[p-(p-nitrobenzoyl)phenoxy]propyl]-4-phenylpyridinium chloride, m.p. 201°–203° C.

(6c) from the bromide of Example (4A)(l) there was obtained 1-[12-(p-nitrobenzoyl)phenoxy]dodecyl]-4-phenylpyridinium chloride, m.p. 146° C.

(6d) from the bromide of Example (4A)(m) there was obtained 1-[3-[p-(p-trifluoromethylbenzoyl)phenoxy]propyl]-4-phenylpyridinium chloride, m.p. 170°–172° C.

EXAMPLE 7

Under analogous conditions to those in Example 3, 9.5 g (20.15 mmol) of (S)-2-hydroxy-3-[p-(p-nitrobenzoyl)phenoxy]propyl p-toluenesulphonate were reacted with 10 g of 4-phenylpyridine in 120 ml of toluene to give 4.6 g of 1-[(R)-2-hydroxy-3-[p-(p-nitrobenzoyl)-phenoxy]propyl]-4-phenylpyridinium chloride, m.p. 238° C., $[\alpha]_D^{20}+43.8°$ (c 0.8%, MeOH), The tosylate starting material was prepared as follows:

(a) 1 g of 4-hydroxy-4'-nitrobenzophenone was added to 8 ml of DMF containing 110 mg of NaH. The mixture was heated at 40°–50° C. for 30 minutes, then treated with 1.29 g of (R)-3-tosyloxy-1,2-propanediol acetonide and a trace of NaI and heated at 150° C. (oil-bath) under argon for 4 hours. After working-up and purification there were obtained 930 mg (64%) of 4-[[(S)-2,2-dimethyl-1,3-dioxolan-4-yl]methoxy]-4'-nitrobenzophenone, m.p. 92°–93° C., $[\alpha]_D^{20}+5.3°$ (c 1%, MeOH).

(b) 0.5 g of the dioxolane of (a) in 5 ml of THF was added to 0.5 ml of a 25% hydrochloric acid solution. After stirring at room temperature for 3 hours and working-up there were obtained 420 mg (95%) of 4-[(R)-2,3-dihydroxypropoxy]-4'-nitrobenzophenone, m.p. 104°–105° C., $[\alpha]_D^{20}-7.17°$ (c 0.6%, MeOH).

(c) 500 mg of the diol of (b) in 7.5 ml of methylene dichloride were added to 0.75 ml of pyridine and 299 mg of tosyl chloride. After stirring at room temperature for 24 hours and working-up there were obtained 500 mg (67%) of the desired tosylate, $[\alpha]_D^{20}+4.99°$ (c 0.8%, MeOH).

EXAMPLE A

Tablets having the following composition can be manufactured in a manner known per se:

|  | Content per tablet |
| --- | --- |
| Salt of formula I | 200 mg |
| Microcrystalline cellulose | 155 mg |
| Maize starch | 25 mg |
| Talc | 25 mg |
| Hydroxypropylmethylcellulose | 20 mg |
|  | 425 mg |

We claim:
1. A polycyclic salt of the formula

$$A^-XN^+CH_2-(Y)_n-(CH_2)_p-(Z)_q-L-(T)_r-M \qquad 1$$

wherein
$A^-$ is an anion of a strong organic or inorganic acid:
$XN^+$ is pyridinium substituted by $R^1$, $R^2$ and $R^3$;
n, q and r individually are the integer 1 or 0 and p is an integer from 1 to 15;
Y is $CH_2$, $C(H,OH)$ or $C(O)$;
Z is O, S, $CH_2$, C(O), $NQ^1$, $SO_2$, C(O)O, OC(O), $C(O)N(Q^1)$ or $N(Q^1)O(O)$;
L is p-phenylene substituted by $R^4$; and
M is phenyl substituted by $R^5$ and $R^6$,
T has one of the meanings given above, for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
$R^1$ is a group Ar, Ar—$C_{1-4}$—alkyl, ArO or ArC(O),
Ar is phenyl substituted by $R^7$, $R^8$ and $R^9$;
$R^2$ and $R^3$ individually are H, $C_{1-4}$—alkyl, $C_{1-4}$—alkoxy or $C_6H_5$,
$R^4$, $R^5$, $R^6$, $R^7$, $R^8$ and $R^9$ individually are H, halogen, $CF_3$, $NO_2$, CN, $C_{1-4}$—(alkyl, alkoxy, alkylthio or alkylsulphonyl), $SO_2N(R,Q)$, $C(O)N(Q^4,Q^5)$, $C(O)Q^4$, $C(O)OQ^4$ or $OC(O)Q^4$,
R, Q, $Q^1$, $Q^2$ and $Q^3$ individually are H or $C_{1-4}$—alkyl, and
$Q^4$ and $Q^5$ individually are $C_{1-4}$—alkyl.

2. The salt of claim 1, wherein Y is hydroxymethylene.

3. The salt according to claim 1, wherein $XN^+$ is pyridinium substituted in the para-position by $R^1$.

4. The salt of claim 1, wherein $A^-$ is $Cl^-$ or $Br^-$; $XN^+$ is p-phenylpyridinium or p-benzoylpyridinium; p is the integer 1, 2, 8 or 11; q is the integer 1; n and r individually are the integer 1 or 0; Y is CHOH; Z is O, S, NH or C(O)NH; $R^4$, $R^5$ and $R^6$ individually are H; and T is C(O), O, S, $SO_2$, $CH_2$, $C_2H_4$, NH, $C(O)CH_2$ or NHC(O).

5. The salt of claim 1, wherein $A^-$ is $Cl^-$ or $Br^-$; $XN^+$ is p-phenylpyridinium or p-benzoylpyridinium; p is the integer 1, 2, 8 or 11; q is the integer 1; n and r individually are the integer 1 or 0; Y is CHOH; Z is O, S, NH or C(O)NH; $R^6$ is H; $R^4$ is $CH_3$; $R^5$ is F, Cl, Br, $CF_3$, $NO_2$, CN, $OCH_3$ or $SO_2CH_3$ in the para-position to $(T)_r$; and T is C(O), O, S, $SO_2$, $CH_2$, $C_2H_4$, NH, $C(O)CH_2$ or NHC(O).

6. The salt of claim 1, 1-[2-hydroxy-3-[p-(p-nitrobenzoyl)phenoxy]propyl]-4-phenylpyridinium chloride.

7. The salt of claim 1, 1-[12-(p-phenethylphenoxy)dodecyl]-4-phenylpyridinium chloride.

8. The salt of claim 1, 1-[3-[p-[(p-chlorophenyl)thio]phenoxy]-2-hydroxypropyl]-4-phenylpyridinium chloride.

9. The salt of claim 1, 1-[3-[p-(p-cyanobenzoyl)phenoxy]-2-hydroxypropyl]-4-phenylpyridinium chloride.

10. The salt of claim 1, 1-[9-(p-phenethylphenoxy)nonyl]-4-phenylpyridinium bromide.

11. A pharmaceutical composition comprising a about 30% to about 70% of a salt of the formula

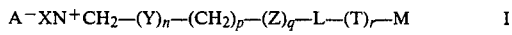

$$A^- XN^+ CH_2-(Y)_n-(CH_2)_p-(Z)_q-L-(T)_r-M \qquad I$$

wherein $A^-$ is an anion of a strong organic or inorganic acid;
$XN^+$ is pyridinium substituted by $R^1$, $R^2$ and $R^3$;
n, q and r individually are the integer 1 or 0 and p is an integer from 1 to 15;
Y is $CH_2$, C(H,OH) or C(O);
Z is O, S, $CH_2$, C(O), $NQ^1$, $SO_2$, C(O)O, OC(O), $C(O)N(Q^1)$ or $N(Q^1)C(O)$;
L is p-phenylene substituted by $R^4$; and
M is phenyl substituted by $R^5$ and $R^6$,
T has one of the meanings given above, for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
$R^1$ is a group Ar, Ar—$C_{1-4}$—alkyl, ArO or ArC(O), Ar is phenyl substituted by $R^7$, $R^8$ and $R^9$;
$R^2$ and $R^3$ individually are H, $C_{1-4}$—alkyl, $C_{1-4}$—alkoxy or $C_6H_5$,
$R^4$, $R^5$, $R^6$, $R^7$, $R^8$ and $R^9$ individually are H, halogen, $CF_3$, $NO_2$, CN, $C_{1-4}$—(alkyl, alkoxy, alkylthio or alkylsulphonyl, $SO_2N(R, Q)$, $C(O)N(Q^4,Q^5)$, $C(O)Q^4$, $C(O)OQ^4$ or $OC(O)Q^4$,
R, Q, $Q^1$, $Q^2$ and $Q^3$ individually are H or $C_{1-4}$—alkyl, and
$Q^4$ and $Q^5$ individually are $C_{1-4}$—alkyl, in a pharmaceutically effective amount for inhibiting the intestinal resorption of cholesterol or of bile salts in the enterohepatic circulation; and (b) 70% to about 30%, respectively, of a pharmaceutically acceptable carrier material, said composition being in a unit dosage form.

12. The composition of claim 11, wherein said composition is in an oral unit dosage form.

13. The composition of claim 12, wherein the salt is 1-[2-hydroxy-3-[p-(p-nitrobenzoyl)phenoxy]propyl]-4-phenylpyridinium chloride.

14. The composition of claim 11, wherein the salt is 1-[12-(p-phenethylphenoxy)dodecyl]-4-phenylpyridinium chloride.

15. The composition of claim 11, wherein the salt is 1-[3-[p-[(p-chlorophenyl)thio]phenoxy]-2-hydroxypropyl]-4-phenylpyridinium chloride.

16. The composition of claim 11, wherein the salt is 1-[3-[p-(p-cyanobenzoyl)phenoxy]-2-hydroxypropyl]-4-phenylpyridinium chloride.

17. The composition of claim 11, wherein the salt is present in a pharmaceutically effective amount for inhibiting intestinal resorption of cholesterol or a bile salt.

18. A method of inhibiting the intestinal resorption of cholesterol or of a bile salt in a mammal, comprising administering to the mammal a salt of the formula

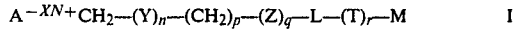

$$A^- XN^+ CH_2-(Y)_n-(CH_2)_p-(Z)_q-L-(T)_r-M \qquad I$$

wherein $A^-$ is an anion of a strong organic or inorganic acid;
$XN^+$ is pyridinium substituted by $R^1$, $R^2$ and $R^3$;
n, q and r individually are the integer 1 or 0 and p is an integer from 1 to 15;
Y is $CH_2$, C(H,OH) or C(O);
Z is O, S, $CH_2$, C(O), $NQ^1$, $SO_2$, C(O)O, OC(O), $C(O)N(Q^1)$ or $N(Q^1)C(O)$;
L is p-phenylene substituted by $R^4$; and
M is phenyl substituted by $R^5$ and $R^6$,
T has one of the meanings given above, for Z or is $C(CH_3)_2$, $C_2H_4$, $C(Q^2)=C(Q^3)$, $C\equiv C$, $CH_2C(O)$, $C(O)CH_2$, $CH_2O$ or $OCH_2$,
$R^1$ is a group Ar, Ar—$C_{1-4}$—alkyl, ArO or ArC(O), Ar is phenyl substituted by $R^7$, $R^8$ and $R^9$;
$R^2$ and $R^3$ individually are H, $C_{1-4}$—alkyl, $C_{1-4}$—alkoxy or $C_6H_5$,
$R^4$, $R^5$, $R^6$, $R^7$, $R^8$ and $R^9$ individually are H, halogen, $CF_3$, $NO_2$, CN, $C_{1-4}$—(alkyl, alkoxy, alkylthio or alkylsulphonyl, $SO_2N(R,Q)$, $C(O)N(Q^4,Q^5)$, $C(O)Q^4$, $C(O)OQ^4$ or $OC(O)Q^4$,
R, Q, $Q^1$, $Q^2$ and $Q^3$ individually are H or $C_{1-4}$—alkyl, and p1 $Q^4$ and $Q^5$ individually are $C_{1-4}$—alkyl.

* * * * *

UNITED STATES PATENT AND TRADEMARK OFFICE
CERTIFICATE OF CORRECTION

PATENT NO. : 4,675,328

DATED : June 23, 1987

INVENTOR(S) : Jean-Marie Cassal, Albrecht Edenhofer, Henri Ramuz

It is certified that error appears in the above-identified patent and that said Letters Patent is hereby corrected as shown below:

In Claim 11, line 2, "a about" shoud be -- a) about --.

In Claim 18, formula I, "$A^{-XN+}$", should be -- $A^-XN^+$ --.

In Claim 18, last line, delete "p1".

Signed and Sealed this

Twenty-sixth Day of July, 1988

Attest:

DONALD J. QUIGG

Attesting Officer      Commissioner of Patents and Trademarks